US011455505B2

(12) United States Patent
Ho

(10) Patent No.: US 11,455,505 B2
(45) Date of Patent: Sep. 27, 2022

(54) INJECTION VIAL MANAGEMENT SYSTEM

(71) Applicant: AI Bioelectronic Healthtech Co., Ltd., Taoyuan (TW)

(72) Inventor: Yen-Yi Ho, Taoyuan (TW)

(73) Assignee: AI Bioelectronic Healthcare Co., Ltd., Taoyuan (TW)

( * ) Notice: Subject to any disclaimer, the term of this patent is extended or adjusted under 35 U.S.C. 154(b) by 0 days.

(21) Appl. No.: 17/189,424

(22) Filed: Mar. 2, 2021

(65) Prior Publication Data
US 2022/0058456 A1 Feb. 24, 2022

(30) Foreign Application Priority Data
Aug. 21, 2020 (TW) ................. 109128674

(51) Int. Cl.
G06K 7/08 (2006.01)
G06K 19/07 (2006.01)
G16H 20/17 (2018.01)
G16H 70/40 (2018.01)
G16H 20/13 (2018.01)
A61J 1/05 (2006.01)
G06K 7/10 (2006.01)

(52) U.S. Cl.
CPC ............ G06K 19/0723 (2013.01); A61J 1/05 (2013.01); G06K 7/10297 (2013.01); G06K 7/10366 (2013.01); G16H 20/13 (2018.01); G16H 20/17 (2018.01); G16H 70/40 (2018.01); A61J 2205/60 (2013.01)

(58) Field of Classification Search
CPC ........... G06K 19/0723; G06K 7/10297; G16H 20/17; G16H 70/40

USPC ......................................... 235/451
See application file for complete search history.

(56) References Cited

U.S. PATENT DOCUMENTS

| 2013/0245545 | A1* | 9/2013 | Arnold ................ A61M 5/1723 604/66 |
| 2019/0262230 | A1 | 8/2019 | Bentkovski |
| 2020/0289740 | A1* | 9/2020 | Tamtoro ................. A61J 7/0409 |
| 2020/0351094 | A1* | 11/2020 | Canterbury ............ G16H 10/40 |
| 2021/0045972 | A1 | 2/2021 | Zuleta |
| 2021/0138456 | A1* | 5/2021 | Ho .......................... G16Y 40/50 |
| 2021/0154391 | A1* | 5/2021 | Tennican ......... G06K 19/06028 |

FOREIGN PATENT DOCUMENTS

| CN | 109963543 A | 7/2019 |
| WO | WO2019145787 A2 | 8/2019 |
| WO | WO2020165242 A1 | 8/2020 |

* cited by examiner

*Primary Examiner* — Ahshik Kim
(74) *Attorney, Agent, or Firm* — Alan D. Kamrath; Karin L. Williams; Mayer & Williams PC

(57) ABSTRACT

An injection vial and injection vial management system is disclosed, wherein the injection vial is filled with a liquid medicine and signally connected with a blockchain network. The injection vial includes a bottle body and a chipset disposed within the bottle body. The chipset includes an identification label and a blockchain module. The identification label records a manufacturing process, a logistic process and a use process. The blockchain module signal connects to the blockchain network in order to record the manufacturing process, logistic process and use process in the blockchain network.

3 Claims, 4 Drawing Sheets

INJECTION VIAL MANAGEMENT SYSTEM

BACKGROUND OF INVENTION

1. Field of the Invention

The present invention relates generally to an injection vial and injection vial management system, and more particularly to an injection vial with a traceable history of manufacturing, circulation and use and an injection vial and injection vial management system with forgery prevention, positioning, temperature control and tracing functions of the injection vial.

2. Description of Related Art

The injection vial is employed for distributing medicines for disease treatment and vaccinations. To guarantee the drug activity and medication safety of the content of an injection vial, the injection vial must be preserved and transported properly, and forgery, spurious drugs and spurious injections must be prevented. To date, no system that can trace the source, storage and transportation of the injection vial (history from manufacturing side to hospital personnel) has been developed. Therefore, it is necessary to provide an injection vial and injection vial management system which can trace the source, storage and transportation of an injection vial and which can prevent defective temperature control during transportation from degrading the drug or vaccine contained within the injection vial, which could cause adverse drug reactions in patients, and also to provide an injection vial and injection vial management system which can facilitate clarification of which of the manufacturer, logistics carrier and hospital injection storage are responsible if adverse drug reactions arise. It is also necessary to provide a set of complete traceable transportation information, injection information and patient information to solve the problems of the existing technology.

SUMMARY OF THE INVENTION

An objective of the present invention is to provide an injection vial with forgery prevention and the function of tracing the history of circulation, location and temperature control.

Another objective of the present invention is to provide an injection vial management system with forgery prevention and the function of tracing the history of circulation, location and temperature control.

To attain the aforesaid objectives, the injection vial of the present invention is filled with liquid medicine and signally connected with a blockchain network. The injection vial includes a bottle body and a chipset. The chipset is disposed in the bottle body. The chipset is a flexible chip comprising an identification label and a blockchain module, wherein the identification label stores the history of manufacturing, circulation and use of the injection vial, wherein the history of manufacturing, circulation and use includes the pharmaceutical factory manufacturing information, logistics transportation information and hospital patient injection information. The pharmaceutical factory manufacturing information includes the production and manufacturing information of the injection vial, such as the NDC (National Drug Code), serial number, batch number and expiration date of the injection vial. The logistics transportation information includes a temperature control record of the transportation of the injection vial, positioning record in the overall process, logistics car number data and logistics personnel data. The hospital patient injection information includes the name of the medical institution using the injection vial, the doctor using the injection vial, the injection time of the injection vial, the data of the patient injected with the injection vial, the date of birth of the patient injected with the injection vial, vital signs (e.g., blood pressure, heart rate, respiration rate, body temperature, and body weight) of the patient at the time of injection with the injection vial, history of allergic reactions of the patient injected with the injection vial, injection history of the patient injected with the injection vial, family disease history of the patient injected with the injection vial, and history of the present illness and/or genetic sequence of the patient injected with the injection vial. The blockchain module is signally connected with the blockchain network such that the history of manufacturing, circulation and use and the electronic medical record of the patient injected with the injection vial are recorded in the blockchain network.

The present invention also provides an injection vial management system for tracing the circulation history of the injection vial. The injection vial includes a chipset. The chipset includes an identification label and a blockchain module. The injection vial tracking system includes a label reader-writer, which reads the circulation history inside the identification label or imports the circulation history into the identification label, and the blockchain module records the circulation history information in the blockchain network. The injection vial and injection vial management system of the present invention can trace the manufacturing source, storage and transportation of the injection vial so as to enhance the medication safety of patients and medical institutions and to clarify the medical information in the event of adverse drug reactions to the medical injection, providing an efficient program for recalling defective medical vaccine injections, clarifying the responsibility for the adverse drug reactions, determining whether the responsibility should be assigned to the pharmaceutical factory manufacturing side, drug logistics side or hospital doctor side, and protecting the patients' medication safety as the basis of drug injury relief.

DETAILED DESCRIPTION OF THE INVENTION

Figure 1:
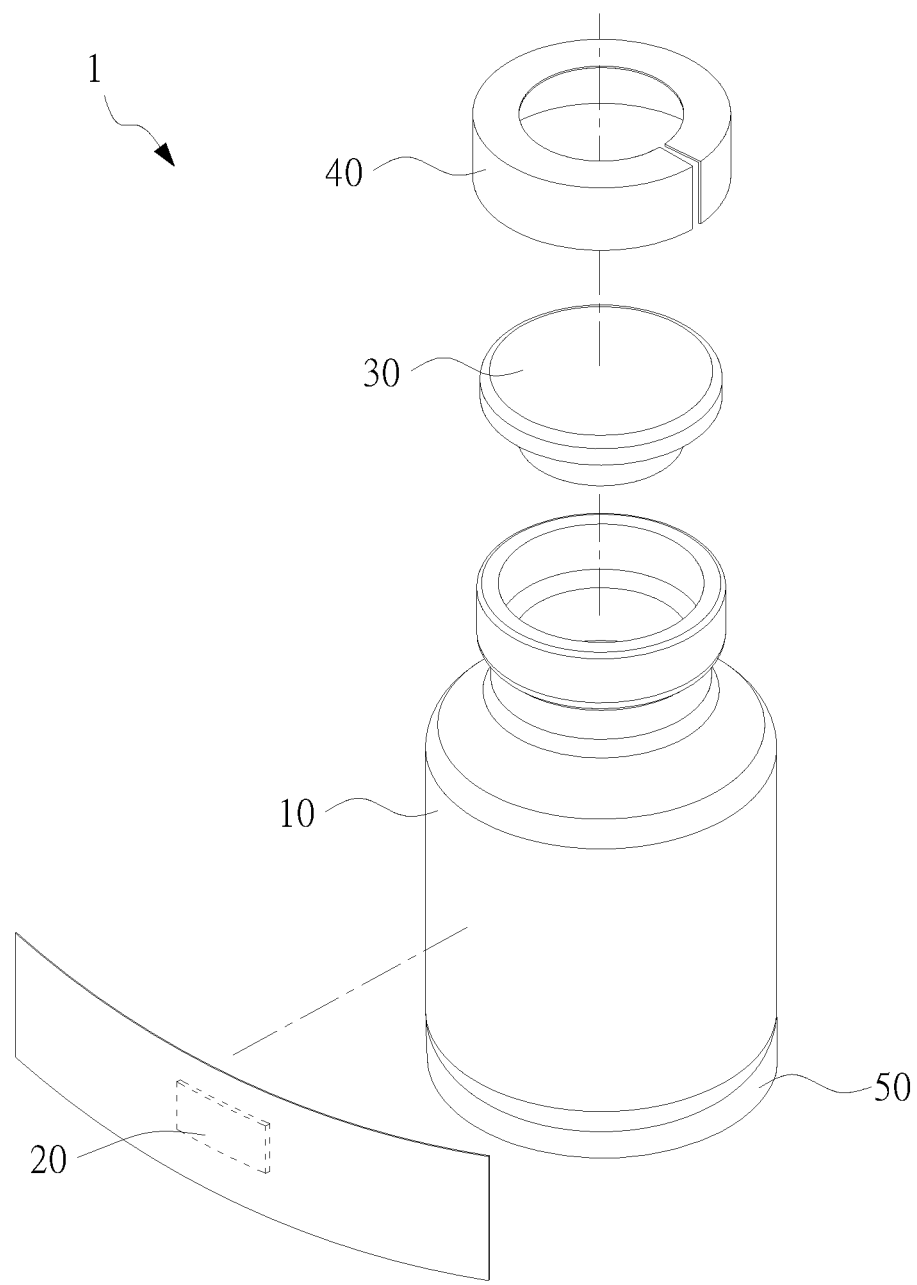
FIG. 1 is an exploded view of an embodiment of the injection vial of the present invention.
Figure 2:
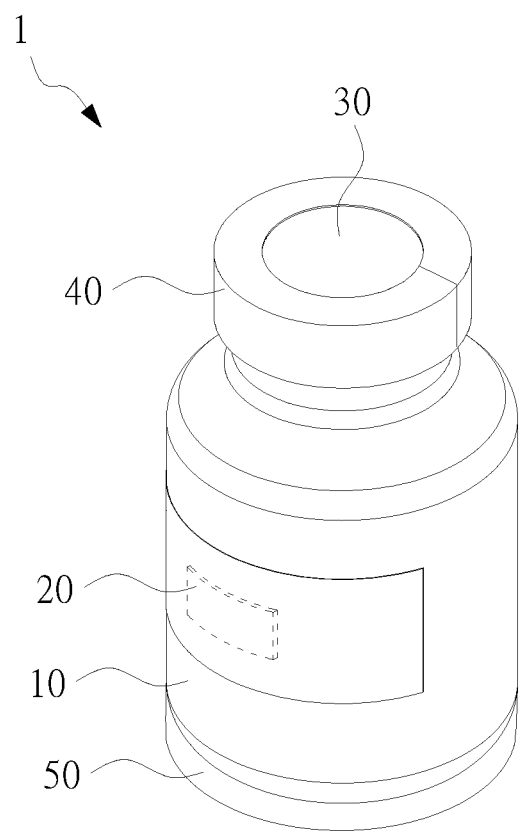
FIG. 2 is a three-dimensional diagram of an embodiment of the injection vial of the present invention.
Figure 3:
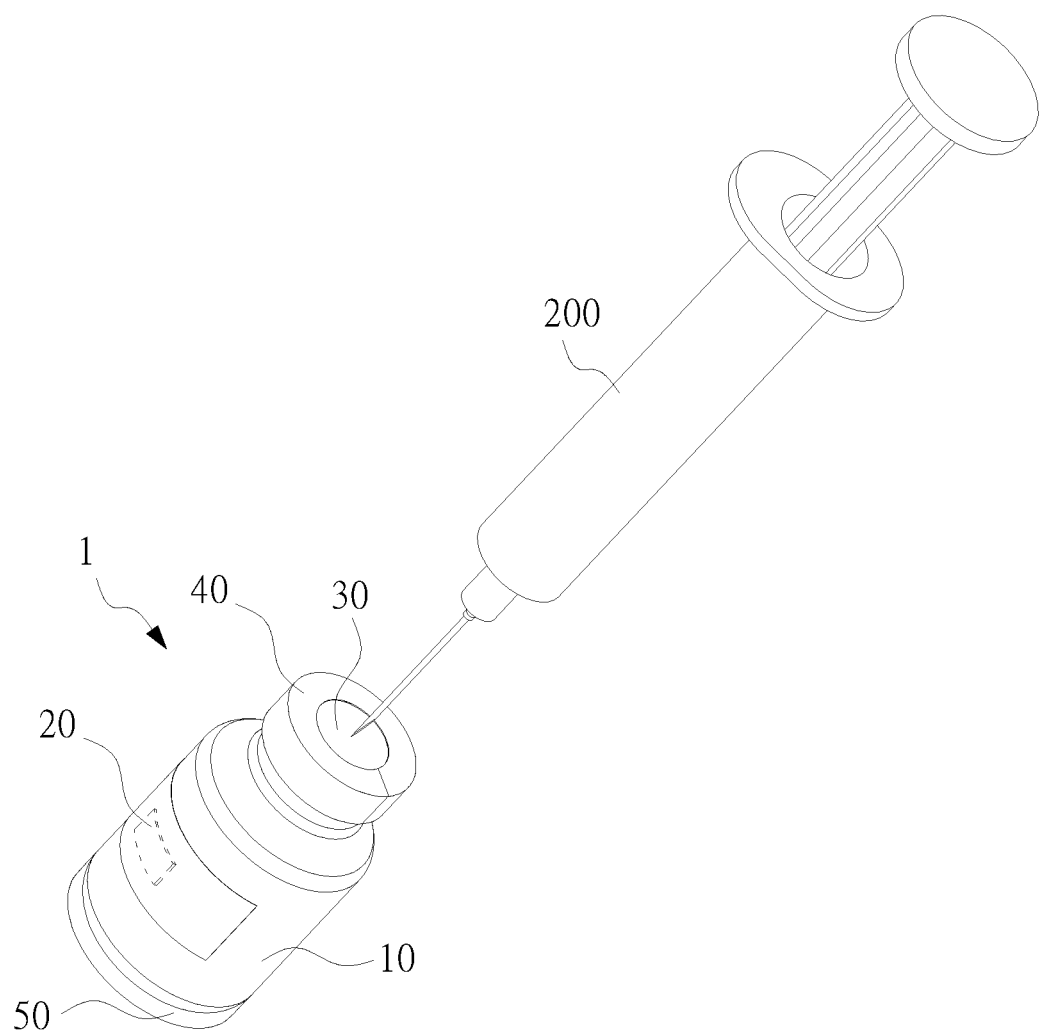
FIG. 3 is a schematic diagram of an embodiment in the operating state of the injection vial of the present invention.

To help the reviewers further understand the technical content of the present invention, the preferred specific embodiments are described below. FIG. 1 to FIG. 4 show an exploded view, a three-dimensional diagram and an operating state diagram of an embodiment of the injection vial of the present invention, as well as the hardware architecture of an embodiment of the injection vial management system of the present invention.

In this embodiment, as shown in FIG. 1 to FIG. 4, the injection vial 1 of the present invention includes a bottle body 10, a chipset 20, a cover 30, an aluminum seal 40 and a battery 50, wherein the chipset 20 is a flexible chip which is disposed in the bottle body 10. The cover 30 covers the bottle body 10. The aluminum seal 40 seals the cover 30 on the bottle body 10. The injection vial 1 of the present invention can be filled with a liquid medicine, and medical personnel can pierce the cover 30 with a syringe 200 so that the liquid medicine can be extracted and injected into the patient. It shall be noted that the injection vial 1 of the present invention can contain a drug or a vaccine.

Figure 4:
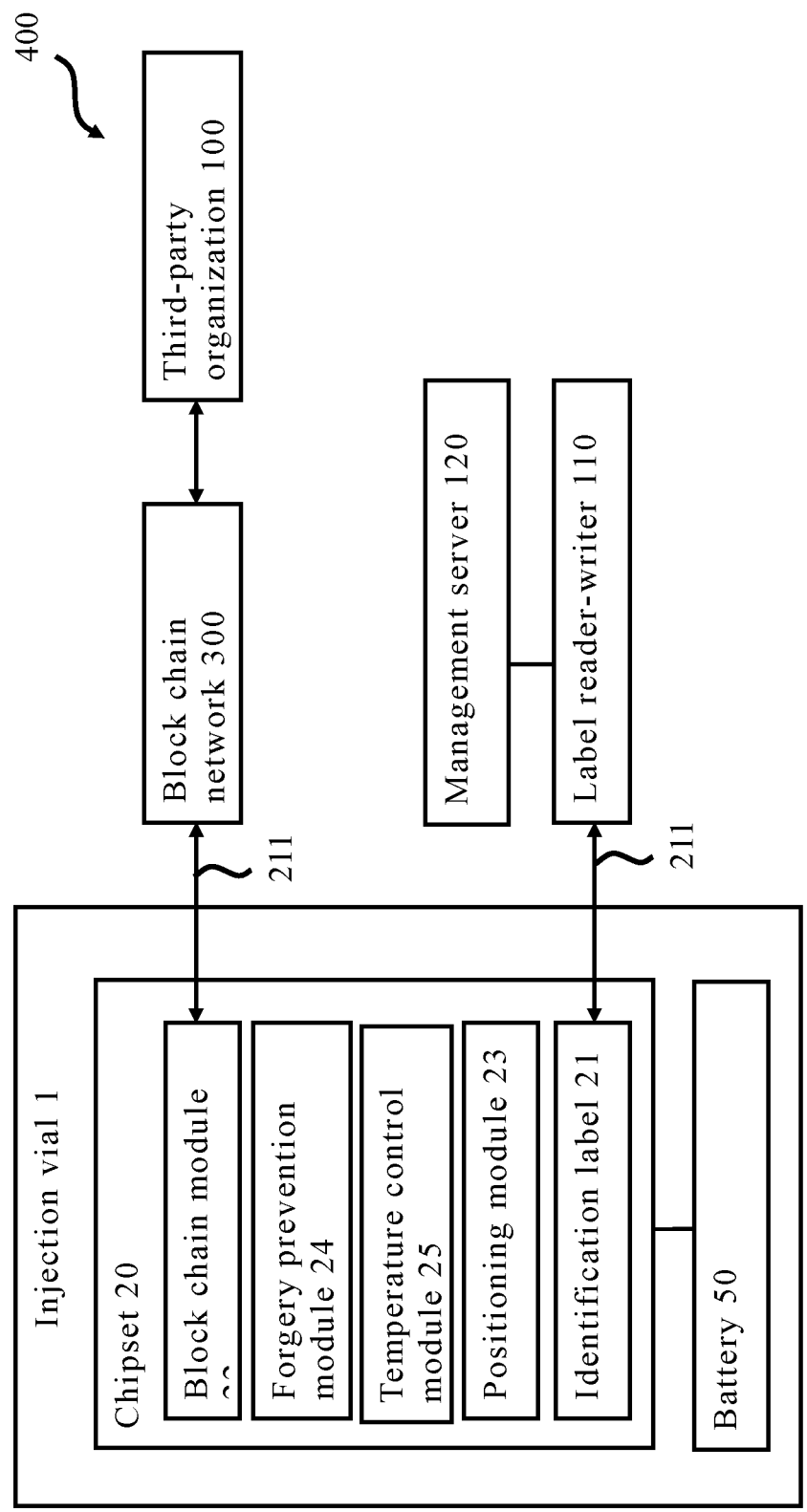
FIG. 4 shows the hardware architecture of an embodiment of the injection vial management system of the present invention.

As shown in FIG. 1 and FIG. 4, the chipset 20 of the present invention includes an identification label 21, a blockchain module 22, a positioning module 23, a forgery prevention module 24 and a temperature control module 25. The identification label 21 stores the history of manufacturing, circulation and use 211 of the injection vial 1. The blockchain module 22 is signally connected with the identification label 21 and a blockchain network 300 such that the history of manufacturing, circulation and use 211 and the electronic medical record of the patient injected with the injection vial are recorded in the blockchain network 300. According to a specific embodiment of the present invention, the identification label 21 is a Radio Frequency Identification (RFID) label or an NFC label. The blockchain module 22 includes an operation chip and a wireless communication chip or a communication antenna, and the source and history of the injection vial 1 and the electronic medical record of the patient injected with the injection vial are recorded in the blockchain network 300, and to ensure the traceability and unlikely falsification of a record of the blockchain 300, the manufacturing history 211 of the injection vial 1 is recorded and traced, wherein the history of manufacturing, circulation and use 211 includes pharmaceutical factory manufacturing information, logistics transportation information and hospital patient injection information. The pharmaceutical factory manufacturing information includes the production and manufacturing information of the injection vial, such as the NDC, serial number, batch number and expiration date of the injection vial. The logistics transportation information includes the temperature control record throughout the transportation of the injection vial, the positioning record of the overall process, logistics car number data and logistics personnel data. The hospital patient injection information includes the name of the medical institution using the injection vial, the doctor using the injection vial, the injection time of the injection vial, the data of the patient injected with the injection vial, the date of birth of the patient injected with the injection vial, the vital signs (e.g., blood pressure, heart rate, respiration rate, body temperature, and body weight) of the patient injected with the injection vial at the time of injection, the history of allergic reactions of the patient injected with the injection vial, the injection history of the patient injected with the injection vial, the family disease history of the patient injected with the injection vial, and the history of the present illness and/or genetic sequence of the patient injected with the injection vial. The positioning module 23 is a Global Positioning System (GPS) chip, and the injection vial 1 is positioned by the positioning module 23 so as to determine the current position of the injection vial 1 and to record the relationship between the transportation process and time points in the overall process, transportation time and transportation route. In this embodiment, the forgery prevention module 24 is a forgery prevention label, and the temperature control module 25 is a chip with a temperature induction function. The temperature control module 25 detects and monitors the temperature of the injection vial 1 so as to monitor whether the injection vial 1 is at an appropriate temperature or not to prevent overheating from influencing the activity of the drug or vaccine contained in the injection vial 1. According to a specific embodiment of the present invention, the injection vial 1 includes a battery 50, and the battery 50 is disposed in the bottle body 10 to supply power to the chipset 20 so as to guarantee normal operation of the chipset 20.

According to a specific embodiment of the present invention, the injection vial 1 of the present invention can include a 2D bar code on the outer surface of the chipset 20 so that a patient or medical institution can scan the 2D bar code to read the history of manufacturing, circulation and use 211 of the injection vial so as to guarantee the safety and record of the patient in the overall process of vaccination or drug injection.

As shown in FIG. 1 and FIG. 4, according to a specific embodiment of the present invention, the injection vial 1 of the present invention can be signally connected with a blockchain network 300 so as to record the history of manufacturing, circulation and use 211 of the injection vial 1 and the electronic medical record of the patient injected with the injection vial, and a third-party organization 100 can search for the history of manufacturing, circulation and use 211 of the injection vial 1 and the electronic medical record of the patient injected with the injection vial through the blockchain network 300. According to a specific embodiment of the present invention, the third-party organization 100 includes a pharmaceutical factory, a medical institution and a trace-link management server. According to a specific embodiment of the present invention, the injection vial 1 is provided with a label reader-writer 110 to form an injection vial management system 400 so as to transfer the history of manufacturing, circulation and use 211 of the injection vial 1 into the identification label 21 or to read the history of manufacturing, circulation and use 211 of the injection vial 1 in the identification label 21, and to manage and trace the history of manufacturing, circulation and use 211 of the injection vial 1. In this embodiment, the label reader-writer 110 is an RFID label reader-writer or an NFC label reader-writer. According to another specific embodiment of the present invention, the label reader-writer 110 can be signally connected with the management server 120 such that the management server 120 can transfer the history of manufacturing, circulation and use 211 of the injection vial 1 to the label reader-writer 110 and the label reader-writer 110 can write the history of manufacturing, circulation and use 211 in the identification label 21, or the management server 120 receives the history of manufacturing, circulation and use 211 read by the label reader-writer 11. According to a specific embodiment of the present invention, the label reader-writer 110 can be directly arranged in the medical institution, pharmaceutical factory and trace-link management server to provide global drug supply chain tracing data. When the label reader-writer 110 scans the identification label 21, the medical personnel can know the history of manufacturing, circulation and use of the injection vial 1 so as to guarantee the patient's safety, and the hospital patient side and injection information are written in the identification label 21 by the label reader-writer 110 and uploaded to the management server 120.

Additionally, according to a specific embodiment of the present invention, the electronic medical record of the patient injected with the injection vial can be uploaded to the management server 120.

The injection vial 1 and injection vial management system of the present invention can manage and trace the source, storage and transportation of the injection vial so as to enhance the medication safety of patients and medical institutions. The injection vial 1 of the present invention meets the designated minimum sales packaging requirements of prescription injections, and it can enhance the supply chain efficiency, prevent the distribution of illegal and spurious drugs, enhance the program and efficiency of recalling of defective prescription injections, and clarify medical and responsibility attribution issues in drug relief. The injection vial 1 and injection vial management system 400 of the present invention meet the designated minimum sales packaging requirements of prescription injections, which can enhance the supply chain efficiency, prevent the distribution of illegal and spurious drugs, enhance the program and efficiency of recall of defective prescription injections, and clarify medical and responsibility attribution issues in drug relief Additionally, the case history information of patients worldwide who are injected with the injection vial 1 of the present invention can be collected by the injection vial 1 and injection vial management system 400 of the present invention, including the name of the medical institution using the injection vial, the doctor using the injection vial, the injection time of the injection vial, the data of the patient injected with the injection vial, the date of birth of the patient injected with the injection vial, the vital signs (e.g., blood pressure, heart rate, respiration rate, body temperature, and body weight) of the patient injected with the injection vial at the time of injection, history of allergic reactions of the patient injected with the injection vial, injection history of the patient injected with the injection vial, family disease history of the patient injected with the injection vial, and history of the present illness and/or genetic sequence of the patient injected with the injection vial, providing the correlation between vaccine/drugs and genetic sequences for a Big Data database of drug and vaccine injections, database uploads, pharmaceutical factories (manufacturing side), logistics providers (logistics side), hospital (doctor side) and third party backup data side storage analysis, and patient's personal injections and personal storage of the electronic case, matching the spirit of the electronic case of a blockchain.

Although the invention has been explained in relation to its preferred embodiment, it is to be understood that many other possible modifications and variations can be made without departing from the spirit and scope of the invention as hereinafter claimed.

What is claimed is:

1. An injection vial management system for tracing a pharmaceutical factory manufacturing information, a logistics transportation information and a hospital patient injection information of an injection vial, the injection vial comprising a chipset, the chipset comprising an identification label and a blockchain module, the blockchain module comprising an operation chip and a wireless communication chip or a communication antenna for recording the pharmaceutical factory manufacturing information, the logistics transportation information and the hospital patient injection information of the injection vial in the blockchain network, the injection vial management system comprising:

a label reader-writer, which reads or writes the pharmaceutical factory manufacturing information, the logistics transportation information and the hospital patient injection information, and the pharmaceutical factory manufacturing information, the logistics transportation information and the hospital patient injection information are recorded in the blockchain network through the blockchain module, wherein the pharmaceutical factory manufacturing information comprises a production and manufacturing information of the injection vial comprising a NDC, a serial number, a batch number and an expiration date of the injection vial, the logistics transportation information comprises a temperature control record throughout a transportation of the injection vial, a positioning record of the overall process, a logistics car number data and a logistics personnel data, the hospital patient injection information comprises a name of the medical institution using the injection vial, a doctor using the injection vial, an injection time of the injection vial, a data of the patient injected with the injection vial, the date of birth of the patient injected with the injection vial, the vital signs of the patient injected with the injection vial at the time of injection, a history of allergic reactions of the patient injected with the injection vial, an injection history of the patient injected with the injection vial, a family disease history of the patient injected with the injection vial, and a history of the present illness and/or genetic sequence of the patient injected with the injection vial, wherein the vital signs comprise a blood pressure, a heart rate, a respiration rate, a body temperature, and a body weight of the patient.

2. The injection vial management system defined in claim 1, wherein the label reader-writer is an RFID label reader-writer or an NFC label reader-writer.

3. The injection vial management system defined in claim 1, wherein the label reader-writer is signally connected with a management server.

* * * * *